United States Patent [19]
Komatani

[11] Patent Number: 5,570,406
[45] Date of Patent: Oct. 29, 1996

[54] X-RAY ANALYZER SYSTEM AND METHOD OF INCREASING RESPONSE TIME

[75] Inventor: Shintaro Komatani, Miyanohigashi-machi, Japan

[73] Assignee: Horiba, Ltd., Kyoto, Japan

[21] Appl. No.: 503,872

[22] Filed: Jul. 18, 1995

[30] Foreign Application Priority Data

Jul. 30, 1994 [JP] Japan .................................. 6-197615

[51] Int. Cl.$^6$ ............................ G01N 23/223; G01T 1/36
[52] U.S. Cl. .................................. 378/44; 378/45; 378/48
[58] Field of Search ................................. 378/44, 45, 48, 378/46, 86, 88, 90

[56] References Cited

U.S. PATENT DOCUMENTS

| | | | |
|---|---|---|---|
| 5,179,580 | 1/1993 | Komatani et al. ........................ | 378/44 |
| 5,249,216 | 9/1993 | Ohsugi et al. ............................ | 378/44 |
| 5,418,826 | 5/1995 | Sato et al. ................................ | 378/48 |

OTHER PUBLICATIONS

"Model SLFA–1800 Fluorescent X–Ray Analyzer for Sulfur in Oil", by Y. Okada, Horiba, Ltd., Readout No. 5, Jul. 1992.

Primary Examiner—Don Wong
Attorney, Agent, or Firm—Price, Gess & Ubell

[57] ABSTRACT

A method and apparatus for determining the concentration of an element in a sample with a fluorescent X-ray qualitative analytical procedure is provided. An X-ray tube radiates a sample with primary X-rays to create fluorescent X-rays from elements in the sample. The computer system can have preset conditions for a measurement of a predetermined concentration amount of an element at a predetermined probability of accuracy. The X-rays coming from the sample are detected, and calculations are performed to determine both the concentration of the element and the predetermined probability of accuracy. These values can be compared automatically with the predetermined values and, when the comparison indicates that the calculated concentration of the element meets the predetermined amount or is greater within the predetermined probability of accuracy, the measurement cycle can be stopped, thereby avoiding unnecessary measurement time.

12 Claims, 5 Drawing Sheets

FIG. 3

```
DURING THE MEASUREMENT
MEASURING TIME IS 15 SEC.
CONCENTRATION IS 0.8765 ± 0.1234 wt %
```
—1

FIG. 4

```
DURING THE MEASUREMENT
MEASURING TIME IS 15 SEC.
CONCENTRATION IS 0.8765 ± 0.1234 wt %
STOP
```
—11

FIG. 5

```
DURING THE MEASUREMENT
MEASURING TIME IS 15 SEC.
CONCENTRATION IS 0.8765 wt %
(0.7531 TO 0.9999 wt %)
```
—21

X-RAY ANALYZER SYSTEM AND METHOD OF INCREASING RESPONSE TIME

BACKGROUND OF THE INVENTION

1. Field of the Invention

The present invention relates to a fluorescent X-ray analyzer and method of determining the concentration of elements in a sample with high reliability in a short period of time.

2. Description of Related Art

X-ray analyzers and qualitative analytical procedures for accurately analyzing a sample containing an element that is capable of generating fluorescent X-rays when impacted by primary X-rays have been successfully used. U.S. Pat. No. 5,418,826 is an example of an analytical method. An example of a conventional analytical method is set forth in FIG. 6, wherein the procedures for quantitatively determining the concentration of elements contained in a sample are disclosed. Referring to FIG. 6 in step 301, a measurement (t) is set, and a measuring cycle is started in step 302. Subsequently, a measurement is conducted in step 303 and the measurement cycle is completed after a lapse of time t in step 304. A calculation of the concentration of the elements and an accuracy, based on a standard deviation of calculated results, is performed in step 305. Finally, the results of the concentrations and their accuracy are displayed, for example, on an LCD screen or printed by the use of a printer in step 306. Frequently this method repeats the calculation procedures several times, for example, 2 to 10 times. Alternatively, the measurement can be conducted at one time followed by an estimation from a counting of X-rays to verify the accuracy of the calculated results of the concentrations.

The conventional analytical methods employed, however, have had the following disadvantages:

(1) The calculated results of concentrations are obtained only after expiration of the time t which was set as the measuring time period, as conducted in step 301, so that the analytical method is inferior in increasing the time for measurements.

(2) In addition, the accuracy of calculated results of concentrations is obtained merely after the time t is set, so that, in order to measure the concentrations of the elements contained in the sample accurately, a measuring time must be conservatively set.

The above-described disadvantages will be below-described with reference to one example. In the measurement of sulfur (S) (hereinafter referred to as a concentration of sulfur) contained in fuel oils, such as heavy oil, by the use of a conventional fluorescent X-ray analytical method of this type, the measuring time t as shown in step 301 is set at a first stage of measurement. In order to conduct the measurement accurately, it has been necessary to measure whether the concentration of sulfur contained in the heavy fuel oil sample is the standard value of (1 wt %) or less, which has required a long measuring time t such as 600 seconds. However, although the calculated result of the concentration of sulfur in this sample was found to be 0.9 wt %, it has been found in the present invention that whether this calculated result of concentration is the standard value or less or whether it is not equal to such a value can be sufficiently judged by measuring for only 10 seconds without expressly using the full measuring time t to an extent of 600 seconds.

Accordingly, the industry is still looking for an improved fluorescent X-ray qualitative analytical system and method for determining the concentration of an element in a sample in an efficient manner.

OBJECTS AND SUMMARY OF THE INVENTION

It is an object of the present invention to provide a fluorescent X-ray analytical method and system that is capable of shortening a measuring time period and improving the handling of samples.

In order to achieve the above-described object, a fluorescent analytical method according to the present invention comprises a step of setting predetermined measuring conditions for a sample and then starting a measurement cycle, a step of calculating the concentrations of elements contained in the sample, and an accuracy of the same and completing the measurement cycle when these calculated values amount to predetermined values, and a step of displaying and/or outputting the concentrations and the accuracy level or, alternatively, the maximum value and the minimum value of concentration.

The fluorescent X-ray qualitative analytical method of determining the concentration of an element of a sample includes radiating a sample with X-rays to create fluorescent X-rays from elements in the sample. Conditions are set for a measurement of a predetermined concentration amount of an element at a predetermined probability of accuracy. The fluorescent X-rays that result from an impact of the primary X-rays on the sample are then detected and the detected results are used to calculate the concentration of an element based on the predetermined probability of accuracy. The calculated concentration of the element is compared with the predetermined amount that has been set, and the result can be indicated to the operator when it matches the predetermined amount or less for the desired probability of accuracy. The calculation of the concentration of the element can be automatically stopped when a comparison indicates that the concentration meets the predetermined amount or less at the predetermined probability of accuracy. This result can be displayed along with the probability of accuracy so that the operator can manually stop the calculations. Alternatively, a maximum time period for repetitively calculating the concentration of an element based on the predetermined probability of accuracy can be set and the system can stop automatically when these standards have been met. The present invention also has the capacity of disclosing a maximum and minimum value of concentration of the element within a predetermined time period, and also within the predetermined probability of accuracy.

The fluorescent X-ray quantitative analytical system can include a source of X-rays for contacting the sample to generate the fluorescent X-rays. A detector that is biased to a particular voltage can detect the fluorescent X-rays which can then be amplified and converted from an analog to a digital signal. A multichannel analyzer can store the detected values of fluorescent X-rays which can be then subsequently processed by an appropriately programmed computer with the results displayed to the operator.

A computer-based monitor can be preset with measurement conditions for a particular sample or samples stored in a random access memory. The accuracy desired is set along with the maximum measurement time period. The monitor can be programmed to automatically calculate the concentration of a sample and its probability of accuracy and then compare it with the predetermined values that are stored in a random access memory. When these values are matched or exceeded, the measurement operation can be terminated and the results can be provided to the operator. Alternatively, the monitor can disclose a maximum and minimum value of concentration of the element within a predetermined time period and also within the predetermined probability of accuracy.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 3 is a diagram showing a display screen of concentrations and probability of accuracy used in the first preferred embodiment;

FIG. 4 is a diagram showing a display screen displaying the concentrations and probability of accuracy used in the second preferred embodiment;

FIG. 5 is a diagram showing a modification of a display screen displaying the concentrations and probability of accuracy for a maximum value and a minimum value;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an efficient X-ray analyzer system and method of increasing a response time of the analyzer system.

Figure 7:
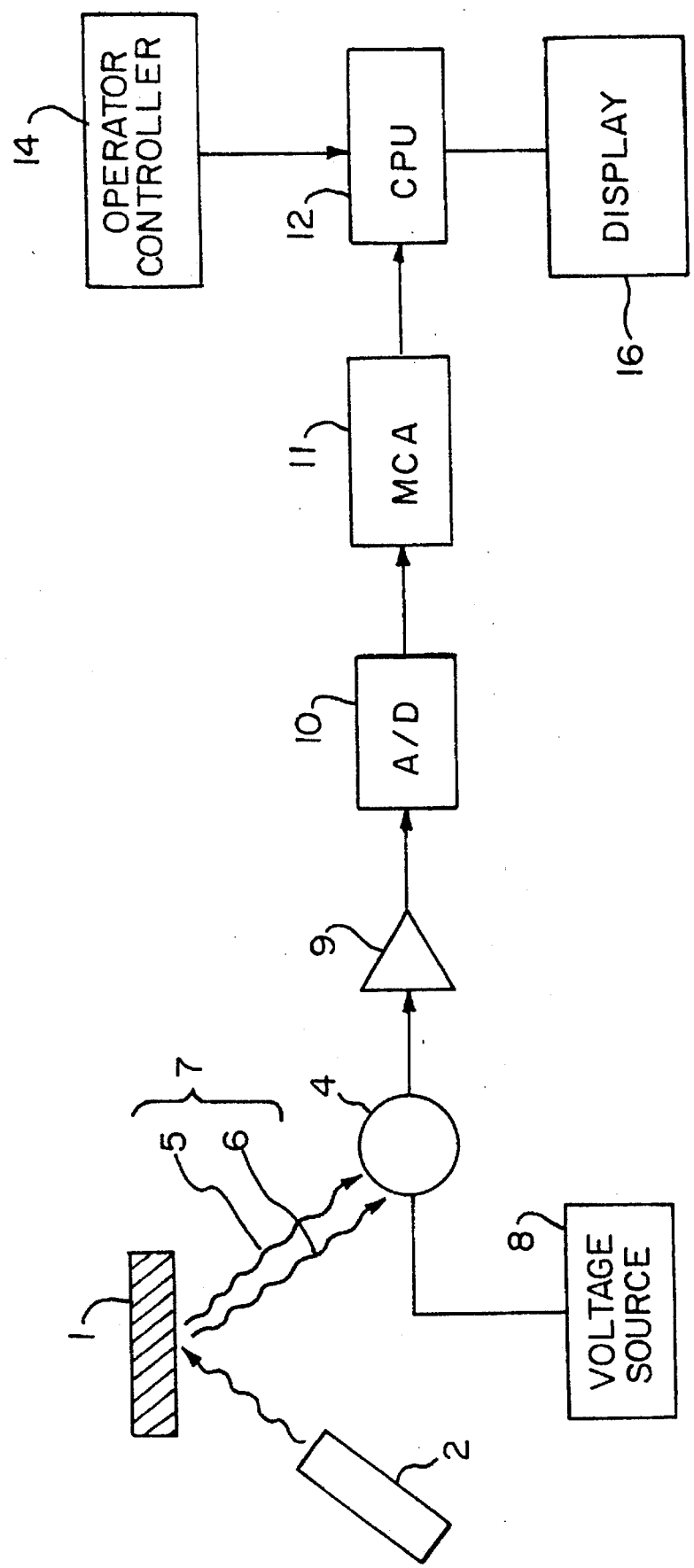
FIG. 7 is a schematic disclosing the X-ray analyzer system which can be used in the present invention.

Referring to FIG. 7, an example of an X-ray analyzer is disclosed which can be programmed to provide the benefits of the present invention. An X-ray tube 2 can direct primary X-rays 3 towards a sample 1. Secondary X-rays 7 such as, for example, fluorescent X-rays 5 and scattered X-rays 6, are emitted from the sample when the primary X-rays 3 are incident upon the sample 1. The secondary X-rays are characteristic of the elements contained in the sample 1. The proportional counter 4 can be operated by applying a predetermined high voltage from a high voltage source 8, and is capable of outputting an (eV) quantity of charges proportional to the energy of the detected X-rays. An amplifier 9 can suitably amplify the output from the proportional counter 4. This output can then be converted by an A/D converter 10 to provide a digital signal. A multichannel analyzer (MCA) 11 is capable of memorizing a predetermined number of output signals from the A/D converter 10 and to carry out a statistical analysis of these stored signals. A CPU 12 is capable of processing the single output from MCA 11 to determine the constituent elements in the sample. An operator controller 14 permits the operator to set conditions for a measurement of a predetermined concentration amount of an element at a predetermined probability of accuracy. The operator can set these conditions for one or more elements which can be stored in a RAM associated with the controller 14. Thus, the operator can subjectively set a predetermined probability of accuracy that is desired for any particular sample run and a maximum measurement time period. A display 16 can display the results of the calculations by the CPU 12, and the operator controller 14 can permit the operator to also manually stop the measurement cycle if the operator determines that the results are satisfactory. A printer (not shown) can be used for providing a hard copy of the analysis.

In an automatic mode of operation, the CPU 12 can be programmed to not only determine the concentration of an element from the measured X-rays 5 and 6, but can further compare the results with the preset measurement values stored in the RAM. When these values are matched or exceeded, the measurement operation can be terminated and the results can be provided to the operator, for example, on a video monitor 16.

As can be appreciated, variations of this X-ray analyzer can be accomplished. Reference is made to U.S. Pat. No. 5,179,580, which is incorporated herein by reference as an example of other features which can be incorporated into the X-ray analyzer.

Figure 1:
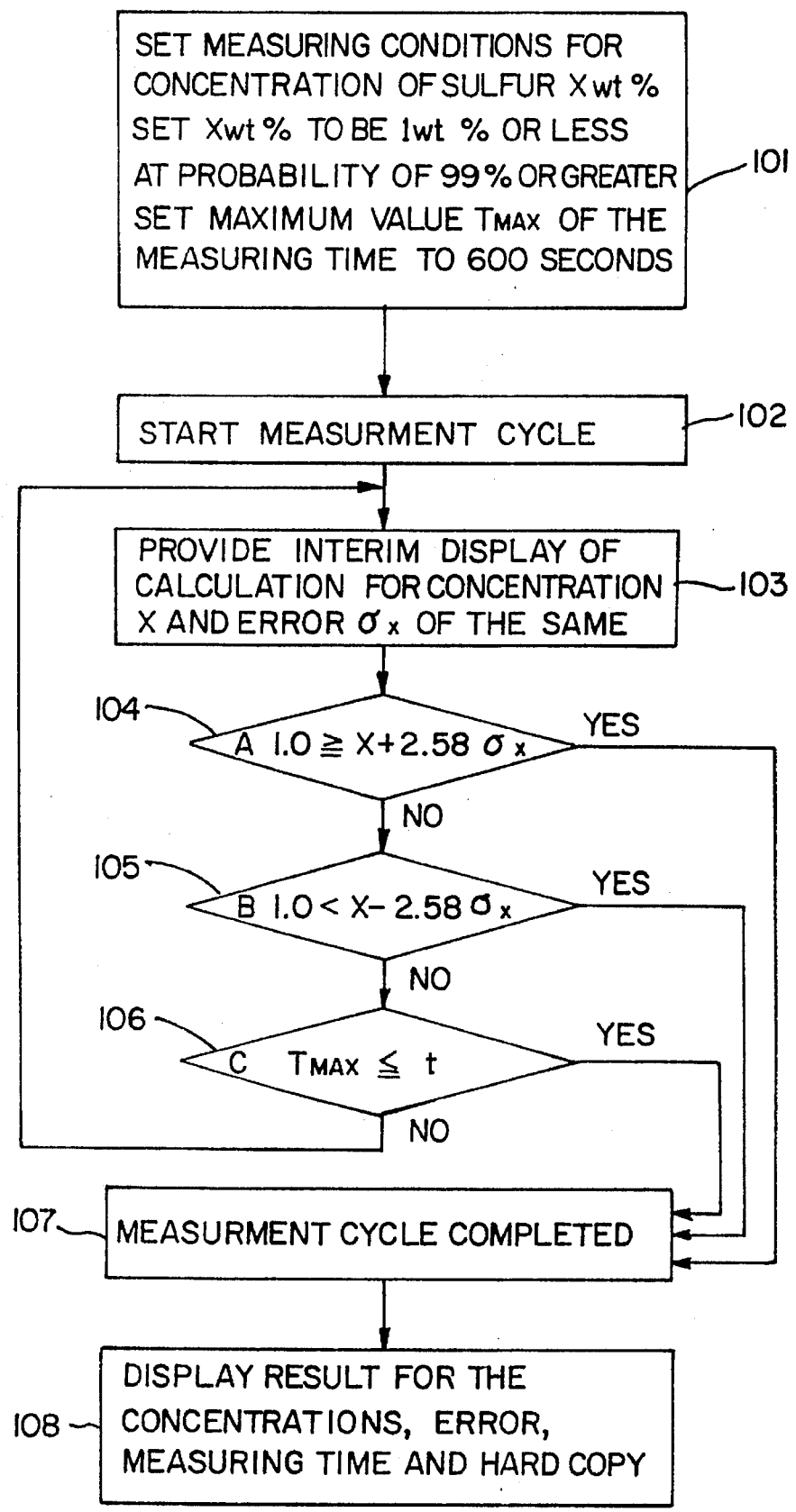
FIG. 1 is a flow chart for describing a first preferred embodiment of the present invention.

Referring to FIG. 1, a flow chart is disclosed setting forth the steps that can be programmed for the CPU 14 to automatically complete a measurement when a calculated value at a desired probability of accuracy is achieved. One possible application of the invention is in measuring the concentration (wt %: X % by weight) of sulfur contained in fuel oils such as heavy oil. As can be appreciated, environmental concerns require a close monitoring of the emission of sulfur into the air. Thus, verifying the sulfur content of a heavy fuel oil to ensure that it meets certain standards is important. Such measurements with a fluorescent X-ray analytical apparatus can be achieved as shown in FIG. 1 by first setting the measuring conditions for the concentration of the desired amount of the sulfur by weight in the fuel oil. This is accomplished in step 101, and can be input into the computer 12 by the operator controller 14. It may also be desired that the maximum measurement time period be set, for example, to 10 minutes or 600 seconds. The measurement cycle is then started at step 102. In step 103, the concentration of sulfur contained in the heavy oil sample and its accuracy or error rate are calculated, as will be subsequently described. For example, the concentration of sulfur X and the accuracy of that specific determination of concentration ($\sigma_x$) is calculated by conducting an operation using the following expressions (1) and (2), respectively:

That is to say, $$X = a \times (F/D) + b \tag{1}$$

wherein a, b are calibration curve constants, D being a counting of scattered X-rays, and F being a counting of fluorescent X-rays characteristic of sulfur. In operation, the values D and F can be determined from a spectrum of energy measured by a proportional counter so that the area of the energy spectrum can be used with appropriate known X-ray filters to distinguish the peaks of the respective X-rays. The calibration curve constants can be derived from measurements of samples of known concentrations of sulfur.

$$\sigma_x = a \times (F/D) \times (1/F + 1/D)^{1/2} + b \tag{2}$$

As a result of these calculations (1) and (2), the concentration X and 2.58 $\sigma_x$ at the present point of time can be displayed on a displaying picture 1 of the LCD at any time, as shown in FIG. 3. In addition, 2.58 is a multiplying value for expanding the range of the sections so as to ensure a probability of 99%.

The value 2.58 is derived from a statistical method and represents a value necessary to achieve a probability of 99% that the sample will have a concentration of sulfur of X=0.8766 in Equation (1). Reference can be made to *Radiation Detection and Measurement* by Glenn F. Knoll, published by John Wiley & Sons, Inc. (1979), incorporated herein by reference, for further information on the statistical derivations of this value. If the desired probability was 90%, then $\sigma_x$ would be multiplied by 1.64. For a probability of 68% the value would be 1, and for a probability of 50% the value would be 0.67.

Repetitively, the above-described calculations of the concentrations and the probability of accuracy for the concentrations are conducted by the CPU 14 to complete the measurement cycle until these calculated values amount to the previously-appointed values so that the results of the concentrations and the accuracy for the same are obtained.

It is judged in step 104 whether the concentration of sulfur X is the standard value (1 wt %) or less at a probability of 99% or more (A). In other words, it is judged from the measuring conditions inputted in step 101 whether the following Equation (3) holds good or not.

$$1.0 \geq X + 2.58\ \sigma_x \tag{3}$$

In the case where it is judged in step 104 that the calculated values are the standard value or less, the measurement is automatically completed (refer to step 107).

On the other hand, in the case where the calculated values are not the standard value or less in step 104, it is judged, as a standard for judging the calculated values, in the following step 105 whether or not the concentration of sulfur X exceeds the standard value (1 wt %) at a probability of 99% or more (B). In other words, it is judged from the measuring conditions inputted in step 101 whether the following Equation (4) holds good or not.

$$1.0 < X - 2.58\ \sigma_x \tag{4}$$

In the case where it was judged in step 105 that the calculated values exceed the standard value, the measurement is automatically completed (refer to step 107).

In the case where it was judged in step 105 that the calculated values do not exceed the standard values, it is judged, as a standard for judging the calculated values, in the following step 106 whether or not the measuring time t exceeds the maximum value $T_{max}$ of 600 seconds (C). Thus, from the measuring conditions inputted in step 101, it is determined if the following Equation (5) holds good or not.

$$T_{max} \leq t\ \text{(measuring time)} \tag{5}$$

In the case where it was judged in step 106 that the measuring time t exceeds 600 seconds, the measurement is automatically completed (refer to step 107).

In summary, if any one of the expressions (3), (4), or (5) holds good, the measurement is automatically completed. In the other cases, the measurement is returned to step 103 to repeat the above-described operation.

Finally, in step 108, the results (concentrations, accuracy [error], measuring time, and the like) are displayed on a displaying picture 1 of an LCD and simultaneously output by means of a printer and an external output.

In the present preferred embodiment, the operator inputs the values to automatically judge the calculated values on the basis of standards (A), (B), and (C), thereby completing the measurement, so that the measuring time can be shortened and the handling (setting of time is not required) can be improved.

Figure 2:
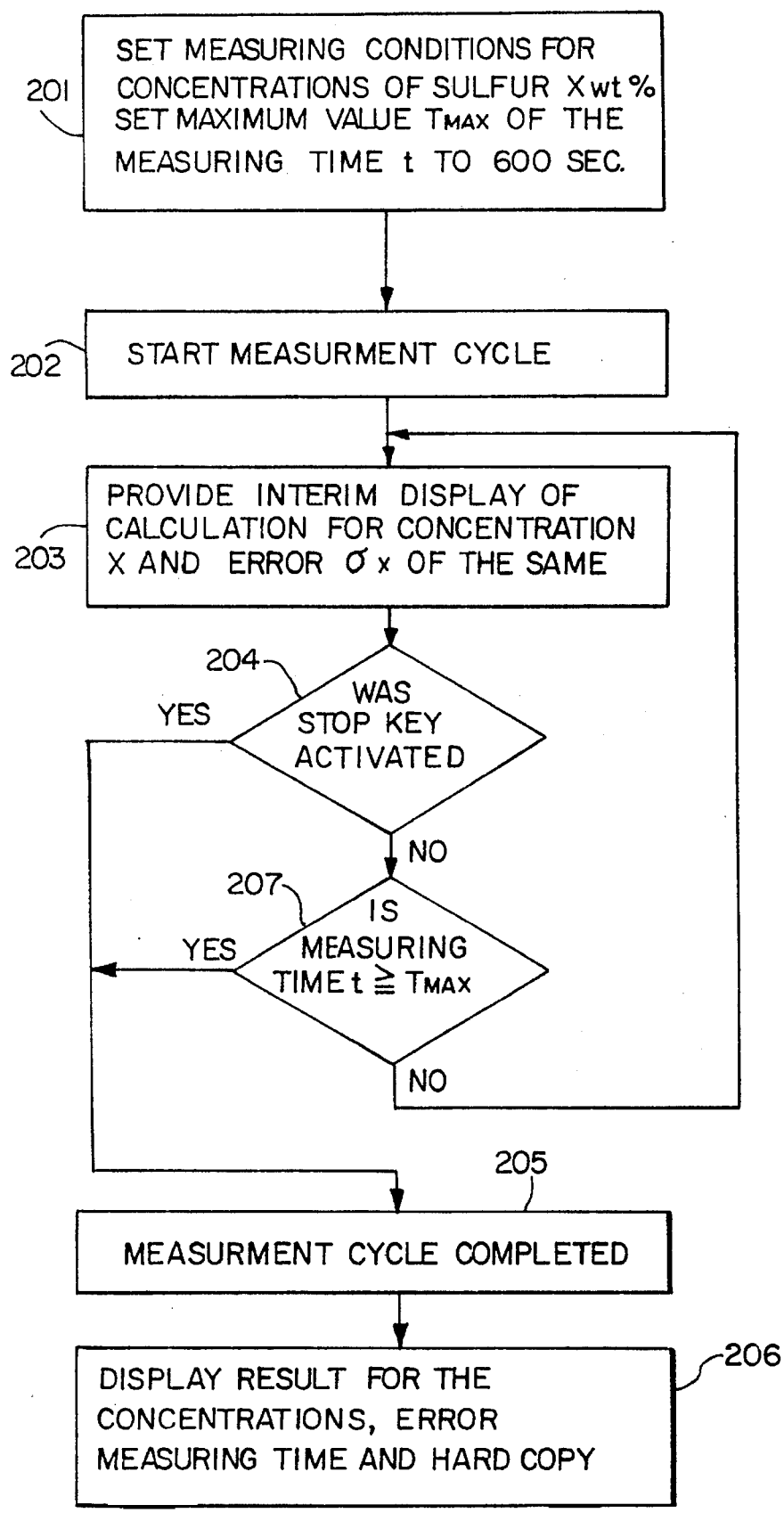
FIG. 2 is a flow chart for describing a second preferred embodiment of the present invention.
Figure 6:
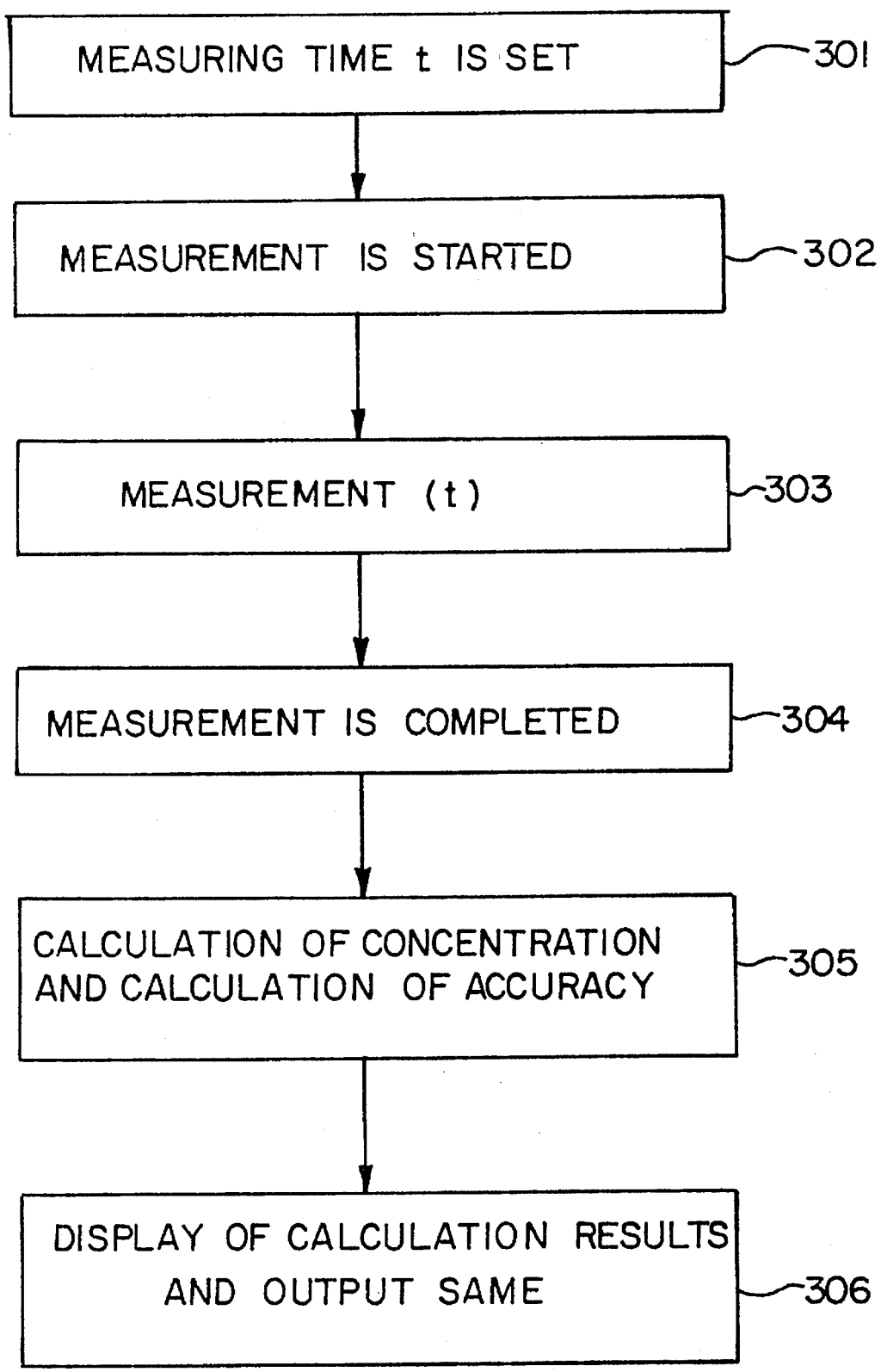
FIG. 6 is a flow chart to illustrate a conventional measurement cycle.

FIG. 2 shows a second preferred embodiment of the present invention in which the operator determines that the predetermined values were displayed on the displaying picture 1 of the LCD (refer to FIG. 4) and pushes a stop key in controller 14 for stopping the measurement.

Predetermined measuring conditions for a heavy fuel oil sample are set in step 201, including a measuring time t of a maximum value $T_{max}$ of 600 seconds or less is inputted, and then the measurement cycle is started (refer to step 202).

In succession to a start of the measurement, a concentration of sulfur X contained in the heavy oil sample and an accuracy (error) for the same are calculated (refer to step 203). At this time, the concentration of sulfur X and the accuracy ($\sigma_x$) for the same is calculated by conducting an operation using the following expressions (1) and (2), respectively.

That is to say, $$X = a \times (F/D) + b \tag{1}$$

wherein a, b are calibration curve constants, D being a counting of scattered X-rays, and F being a counting of sulfur.

$$\sigma_x = a \times (F/D) \times (1/F + 1/D)^{1/2} + b \tag{2}$$

By these operations, the concentration X and 2.58 $\sigma_x$ at that point in time are displayed on a displaying picture 11 of the LCD, as shown in FIG. 4.

Successively, as above-described, calculated values of the concentrations and the accuracy for the same are displayed so that, in the case where the measuring time t does not exceed 600 seconds, if a quantitative value demanded by the operator is obtained from quantitative values (concentration) of midway displays and an accuracy for the same displayed at any time, the operator can push a stop key in step 204 to display "stop," meaning the completion of measurement on the displaying picture 11, thereby completing the measurement cycle (refer to step 205). In step 206, the results (concentrations, accuracy [error], measuring time and the like) are displayed on the displaying picture 11 of the LCD and simultaneously output by means of a printer (not shown) and an external output (refer to step 206).

In the case where the measuring time t exceeds 600 seconds in step 207 while the stop key is not pushed in step 204, the measurement is automatically stopped (refer to step 205).

In the case where the operator may overlook the quantitative result demanded by himself even though it was obtained after, for example, about 10 seconds from the start of the measurement cycle, and he does not push the stop key in step 204, and there is still enough time until the measuring time t of 600 seconds passes in step 207, it can be judged in step 207 that the measuring time t does not exceed the maximum value $T_{max}$ of 600 seconds in the measurement to make the measurement return to step 203, thereby repeating the above-described operation.

As described above, the operator can determine that the value demanded by himself was displayed on the displaying picture 1 of the LCD and push a stop key for stopping the measurement, so that the measuring time can be shortened and the handling (setting of time is not required) can be improved.

In addition, although the concentrations and the accuracy (error) for the same are displayed on the displaying picture 1, 11 of the LCD, respectively, in the above-described preferred embodiments, the maximum value and the minimum value of concentration may also be displayed on a displaying picture 21, as shown in FIG. 5.

As described above, according to the present invention, a fluorescent analytical method comprises the step of setting the measuring conditions for the sample and then starting the measurement, the step of calculating the concentrations of the elements contained in the sample and the accuracy of the same to complete the measurement when these calculated values amount to the appointed values, and the step of displaying and/or outputting the concentrations and the accuracy or the maximum value and the minimum value of concentration, so that the conventional problem that the calculated results of concentrations cannot be obtained until the time set as the measuring time has passed is eliminated. The accuracy of calculated results of concentrations can be obtained merely after the values are achieved rather than the time set so that, in order to accurately measure the concentrations of the elements contained in the sample. A lengthy measuring time can be eliminated and the measuring time can be effectively shortened, while the analytical method can be improved in handling.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A fluorescent X-ray qualitative analytical method of determining the concentration of an element in a sample comprising:

radiating a sample with X-rays to create fluorescent X-rays from elements in the sample;

setting conditions for a measurement of a predetermined concentration amount of an element at a predetermined probability of accuracy;

detecting the fluorescent X-rays resulting from impact of the X-rays with the sample;

calculating from the detected fluorescent X-rays the concentration of the element based on the predetermined probability of accuracy; and comparing the calculated concentration of the element with the predetermined amount and indicating to the operator when it is the predetermined amount or less.

2. The method of claim 1 further including stopping the calculation of the concentration of the element automatically when a comparison indicates the concentration meets the predetermined amount or less at the predetermined probability of accuracy.

3. The method of claim 2 further including displaying the concentration of the element and probability of accuracy and providing means for the operator to manually stop the calculations.

4. The method of claim 1 further including displaying a maximum and minimum value of concentration of the element within a predetermined time period.

5. The method of claim 1 further including setting a maximum time period for repetitively calculating the concentration of the element based on the predetermined probability of accuracy.

6. The method of claim 5 further including stopping the calculation of the concentration of the element automatically when a comparison indicates the concentration meets the predetermined amount or less at the predetermined probability of accuracy.

7. A fluorescent X-ray qualitative analytical system of determining the concentration of an element in a sample comprising:

an X-ray tube for radiating a sample with X-rays to create fluorescent X-rays from elements in the sample;

operator means for setting conditions for a measurement of a predetermined concentration amount of an element at a predetermined probability of accuracy including a computer unit;

a detector for detecting the X-rays resulting from impact of the X-rays with the sample;

means for calculating from the detected X-rays the concentration of the element based on the predetermined probability of accuracy; and means for comparing the calculated concentration of the element with the predetermined amount and indicating to the operator when it is the predetermined amount or less.

8. The system of claim 7 further including means for stopping the calculation of the concentration of the element automatically when a comparison indicates the concentration meets the predetermined amount or less at the predetermined probability of accuracy.

9. The system of claim 8 further including a video monitor for displaying the concentration of the element and probability of accuracy and means for the operator to manually stop the calculations.

10. The system of claim 7 further including means for calculating a maximum and minimum value of concentration of the element within a predetermined time period.

11. The system of claim 7 wherein the operator means sets a maximum time period for repetitively calculating the concentration of the element based on the predetermined probability of accuracy.

12. The system of claim 11 further including means for stopping the calculation of the concentration of the element automatically when a comparison indicates the concentration meets the predetermined amount or less at the predetermined probability of accuracy.

* * * * *